US005671746A

United States Patent [19]

Dreschel et al.

[11] Patent Number: 5,671,746

[45] Date of Patent: Sep. 30, 1997

[54] ELEVATION STEERABLE ULTRASOUND TRANSDUCER ARRAY

[75] Inventors: William Robert Dreschel; Bradley R. Nelson, both of State College; Farley Peechatka, Jr., Port Matilda, all of Pa.

[73] Assignee: Acuson Corporation, Mountain View, Calif.

[21] Appl. No.: 681,793

[22] Filed: Jul. 29, 1996

[51] Int. Cl.[6] .......... A61B 8/00

[52] U.S. Cl. .......... 128/661.01; 128/662.03

[58] Field of Search .......... 128/661.01, 662.03; 73/625, 626; 310/365, 366, 334

[56] References Cited

U.S. PATENT DOCUMENTS

| | | | |
|---|---|---|---|
| 4,448,075 | 5/1984 | Takemura et al. . | |
| 4,570,488 | 2/1986 | Miwa et al. . | |
| 4,580,451 | 4/1986 | Miwa et al. . | |
| 4,671,293 | 6/1987 | Shaulov | 128/662.03 |
| 5,027,820 | 7/1991 | Pesque . | |
| 5,152,294 | 10/1992 | Mochizuki et al. . | |
| 5,167,231 | 12/1992 | Matsui | 128/662.03 |
| 5,327,895 | 7/1994 | Hashimoto et al. . | |
| 5,345,139 | 9/1994 | Gururaja et al. . | |
| 5,410,205 | 4/1995 | Gururaja . | |
| 5,460,179 | 10/1995 | Okunuki et al. . | |
| 5,460,181 | 10/1995 | Seyed-Bolorforosh . | |
| 5,488,956 | 2/1996 | Bartelt et al. | 128/662.03 |
| 5,490,512 | 2/1996 | Kwon et al. . | |

OTHER PUBLICATIONS

McKeighen R. E., "A Compact Concave Array for Cardiac Imaging", 1990 Ultrasonics Symposium, pp. 815–819.

Pendergrass Larry, Gururaja T.R., "Switching in Electrorestrictive Materials", The Seventh US–Japan Seminar on Dielectric and Piezoelectric Ceramics, 1995.

Takeuchi Hiroshi, Masuzawa Hiroshi, Nakaya Chitose, Ito Yujio, "Relaxor Ferroelectric Transducers", 1990 Ultrasonics Sympsium.

Wallace Arden Smith, "The Role of Piezocomposites in Ultrasonic Transducers", 1989 Ultrasonics Symposium, pp. 755–766.

*Primary Examiner*—George Manuel
*Attorney, Agent, or Firm*—Brinks Hofer Gilson & Lione

[57] ABSTRACT

An ultrasonic transducer array for transmitting and receiving ultrasonic energy in multiple two-dimensional imaging planes. The ultrasonic energy in the imaging planes is focused in elevation by the curvature of the transducer array. An imaging plane is selected from a plurality of available imaging planes by electronic switching. Each imaging plane when selected is positioned at a known angle, different from all other imaging planes, due to the known curvature of the transducer array, and the known dimensions of the transducer elements.

16 Claims, 9 Drawing Sheets

Fig. 3
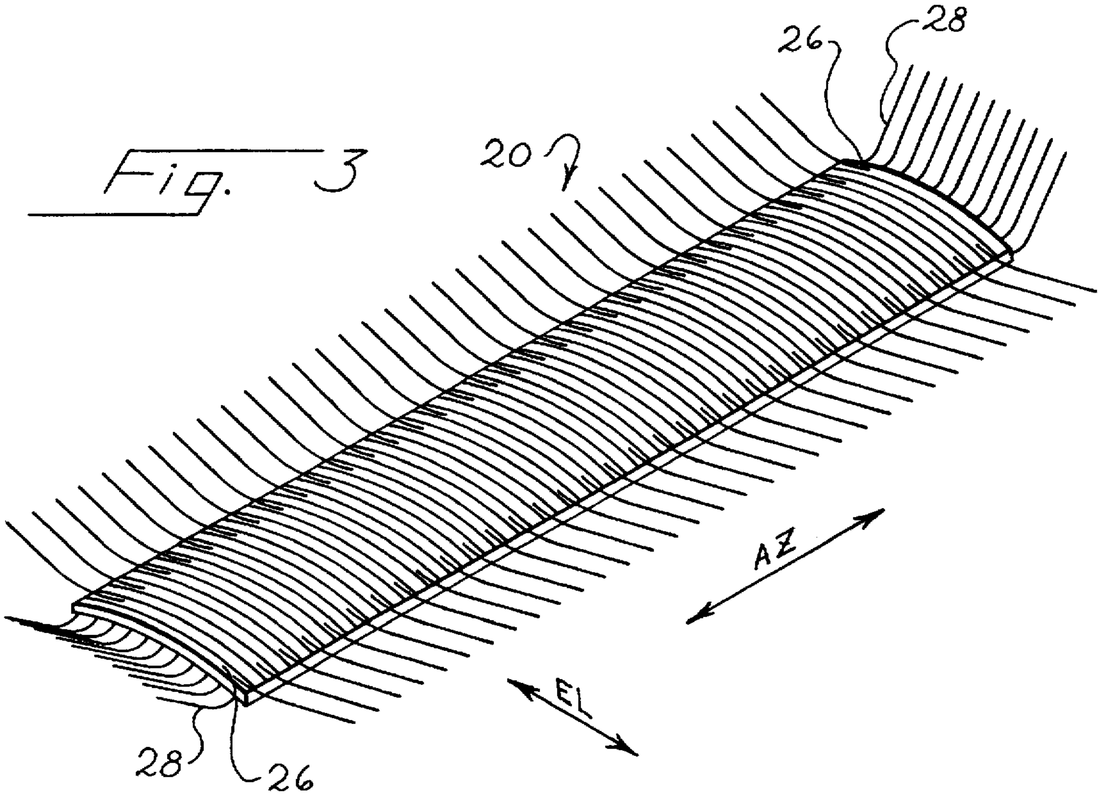
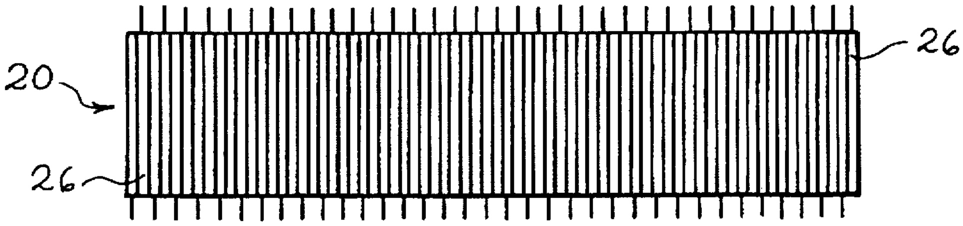
Fig. 4
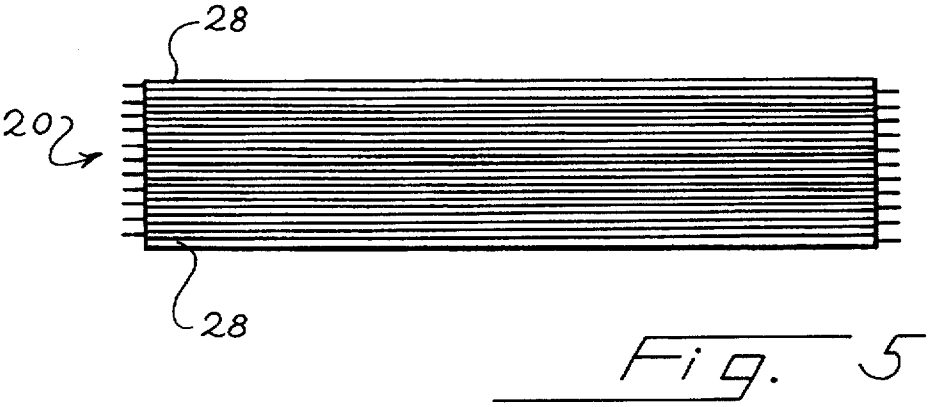
Fig. 5

ELEVATION STEERABLE ULTRASOUND TRANSDUCER ARRAY

FIELD OF THE INVENTION

This invention relates to ultrasound transducers, and more particularly to ultrasound array transducers capable of transmitting and receiving ultrasonic signals in more than one two-dimensional imaging plane.

BACKGROUND OF THE INVENTION

Ultrasonic transducer arrays are used to transmit and receive ultrasonic waves in tissue and organs for medical diagnostic purposes. Ultrasonic transducer arrays convert electrical signals into ultrasonic pressure waves, and conversely convert received echo pressure waves into electrical signals. The received echo waves are used to construct two-dimensional tomographic images of soft tissue, including blood flow.

Many conventional ultrasonic transducer arrays produce usable information from a single two-dimensional imaging plane or slice. Such arrays are typically not suited for the collection of multiple image planes of data for three-dimensional image reconstruction without the addition of positioning or position sensing devices.

Ultrasonic transducer arrays with the capability to collect information useful in reconstructing three-dimensional images typically fall into three categories:

1. Mechanically positioned arrays—In this case a conventional two-dimensional imaging array is translated or rotated to produce sets of image planes with known positions and orientations.
2. Arrays which incorporate position sensing devices—In this case the position of the imaging array in three-dimensional space is recorded by one or more position sensors, and the recorded image planes are reconstructed into three-dimensional images using the position sensor information.
3. Electronically steered ultrasonic transducer arrays—In this case the imaging arrays are typically constructed as two-dimensional arrays of transducer elements, and the imaging system controls the timing of the pulses applied to the transducer elements to steer and focus ultrasonic beams in three-dimensions, and thereby to generate ultrasound information in a plurality of image planes.

SUMMARY OF THE INVENTION

The present invention is directed to an improved ultrasonic transducer that avoids much of the complexity of the prior art transducers and imaging systems discussed above, and which provides image planes which can readily be steered in elevation.

According to a first aspect of this invention, an ultrasonic transducer array comprises a plurality of transducer elements distributed in both an azimuth and an elevation direction, and the transducer elements are arranged to form a concave shape along the elevation direction. A plurality of azimuth electrodes are provided, each coupled to a respective plurality of transducer elements extending along the elevation direction, and a plurality of elevation electrodes are provided, each coupled to a respective plurality of the transducer elements extending along the azimuth direction. As explained below, this array can readily be steered in elevation by properly activating the elevation electrodes.

According to a second aspect of this invention, an ultrasonic transducer is provided comprising a plurality of transducer elements distributed in both the azimuth and the elevation directions. A focusing system is coupled to the transducer elements, and is operative to focus ultrasonic energy radiated by the transducer elements in the elevation direction. A switching circuit is coupled to the transducer elements, and is operative to enable selected sets of the transducer elements. The switching circuit cooperates with the focusing system to steer ultrasonic energy radiated by the selected sets of the transducer elements in the elevation direction.

According to a third aspect of this invention, an ultrasonic transducer comprises transducer elements, azimuth electrodes, and elevation electrodes as described above. A focusing system is coupled to the transducer elements to focus ultrasonic energy radiated by the transducer elements in the elevation direction, and a switching circuit is coupled to the elevation electrodes. The switching circuit activates selected adjacent ones of the elevation electrodes to enable sets of the transducer elements coupled to the selected elevation electrodes, and thereby to steer ultrasonic energy radiated by the transducer elements in the elevation direction.

BRIEF DESCRIPTION OF THE DRAWINGS

FIG. 3 is a perspective view of the transducer array included in the transducer probe of FIGS. 1 and 2.

FIG. 4 is a plan view of the upper side of the transducer array of FIG. 3, showing the azimuth electrodes.

FIG. 5 is a plan view of the lower side of the transducer array of FIG. 3, showing the elevation electrodes.

DETAILED DESCRIPTION OF THE PRESENTLY PREFERRED EMBODIMENTS

Figure 1:
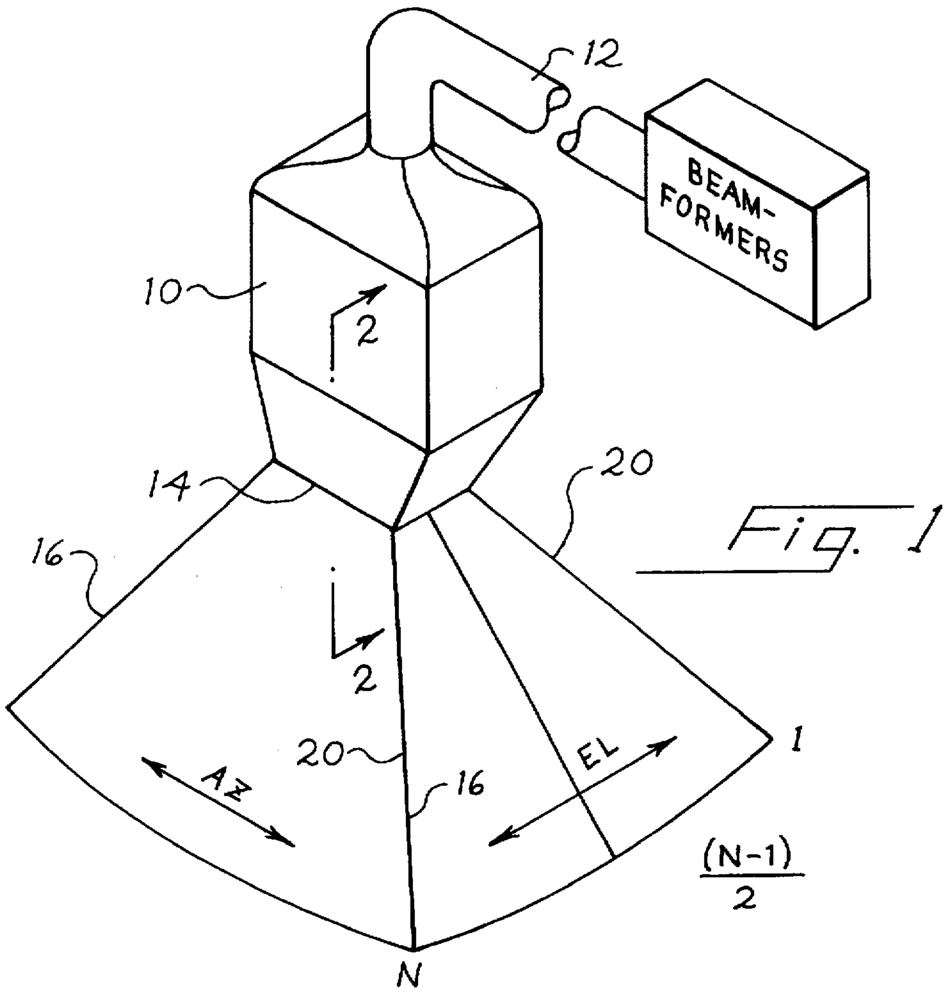
FIG. 1 is a perspective view of a transducer probe which incorporates a presently preferred embodiment of this invention.

Turning now to the drawings, FIG. 1 shows a perspective view of an ultrasonic transducer probe 10 which incorporates a presently preferred embodiment of this invention. The probe 10 is connected by a cable 12 to an imaging system (not shown), which may include conventional transmit and receive beamformers. The probe 10 includes an active region 14 through which ultrasonic energy is radiated into the subject, and through which ultrasonic energy from the subject passes into the probe 10.

In FIG. 1 the reference numeral 16 is used to indicate the limits of the scan region in azimuth, and the reference numeral 20 is used to indicate the limits of the scan region in elevation. The lines marked with reference numerals 16 and 20 are projections of boundaries, and do not represent physical structure. The probe 10 is a fully electronic device that transmits and receives ultrasonic information in a plurality of two-dimensional image planes, making it suitable for three-dimensional ultrasonic imaging applications. The probe 10 provides multiple image planes between the elevation limits 20 by steering the ultrasonic image plane in the elevation direction. In FIG. 1 the symbol 1 is used to indicate the first image plane, the symbol (N−1)/2 is used to indicate the central image plane, and the symbol N is used to indicate the last image plane. These image planes differ in their orientation in the elevation direction.

Figure 2:
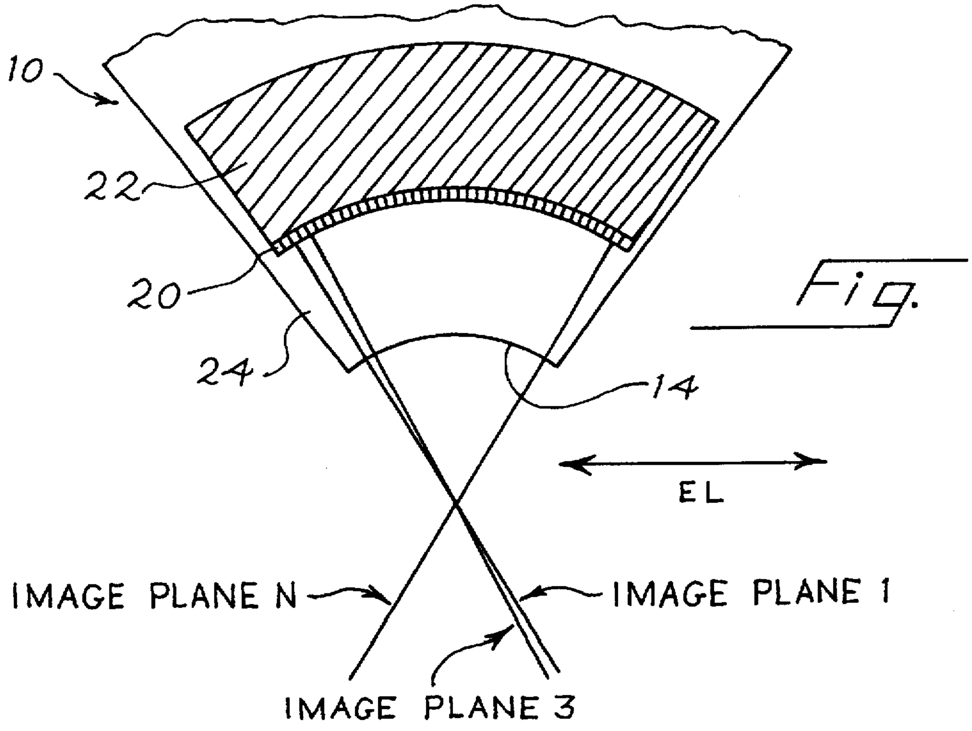
FIG. 2 is a cross-sectional view taken along line 2—2 of FIG. 1.

FIG. 2 is a fragmentary cross section of FIG. 1, showing the transducer array 20 of the probe 10. As explained in greater detail below, the transducer array 20 is made up of a multiplicity of individual transducer elements. The transducer array 20 is mounted in the probe 10 by a backing element 22 which provides a concave curvature to the transducer array along the elevation direction. The backing element 22 is preferably formed of a transducer backing material such as an epoxy, silicone or urethane, typically filled with metal oxides. The backing element 22 serves a number of functions: (1) it provides acoustic damping so that the transducer array 20 does not ring excessively when pulsed; (2) it provides mechanical support to the transducer array 20; and (3) it provides a thermal heat sink to the transducer array 20. A low-attenuation nose piece 24 is included in the probe 10 between the transducer array 20 and the active region 14. This nose piece 24 may, for example, be formed of an RTV silicone or a urethane.

FIG. 2 shows the manner in which the concave curvature of the transducer array 20 focuses and steers ultrasonic energy in the elevation direction. Depending upon which portions of the transducer array are enabled (i.e., the position of the elevation aperture), the image plane can be positioned at a number of discrete planes between image plane 1 and image plane N.

FIG. 3 shows a perspective view of the transducer array 20. As shown in FIG. 3, the transducer array 20 is cylindrically concave, with a substantially constant circular concave shape as measured along the elevation direction. As shown in FIG. 3, the transducer array 20 includes electrodes on both the upper face of the array (the surface facing away from the object being scanned), and on the lower face of array (the surface facing the object being scanned). In this example, the upper electrodes are signal electrodes which are arranged as a plurality of parallel azimuth electrodes 26, each of which extends along the elevation direction, and successive ones of which are distributed along the azimuth direction. The azimuth electrodes 26 will vary in number, depending upon the particular application. By way of example, there can be 32, 64, 128, or more azimuth electrodes 26.

The lower face of the transducer array 20 supports a plurality of control electrodes, that in this embodiment extend parallel to the azimuth direction and are sequentially distributed along the elevation direction. These control electrodes will in this embodiment be referred to as elevation electrodes 28. The number of elevation electrodes will also vary widely, depending on the application. For example, 20, 40 or more elevation electrodes can be used.

FIG. 4 is a plan view showing the arrangement of the azimuth electrodes 26, and FIG. 5 is a plan view showing the orientation of the elevation electrodes 28. The naming convention for the electrodes 26, 28 is for the sake of description, and does not imply that the described orientation of the electrodes 26, 28 is the only usable configuration. For example, the azimuth and elevation electrodes 26, 28 do not have to intersect at right angles, and they may be reversed if desired on the upper and lower faces of the array 20. In general, the azimuth and elevation electrodes are not parallel, such that the elevation electrodes cross successive ones of the azimuth electrodes.

The transducer array 20 is held in a cylindrically concave shape having a constant radius of curvature in the elevation direction by the backing element 22 of FIG. 2. In this embodiment, the elevation electrodes 28 face toward the center of the radius, and the azimuth electrodes 26 face away from the center. The curvature of the transducer array 20 provides two important advantages: (1) it provides a mechanical focusing effect to achieve elevation focus, and (2) it provides the desired angular offset between separate ones of the imaging planes.

Figure 6:
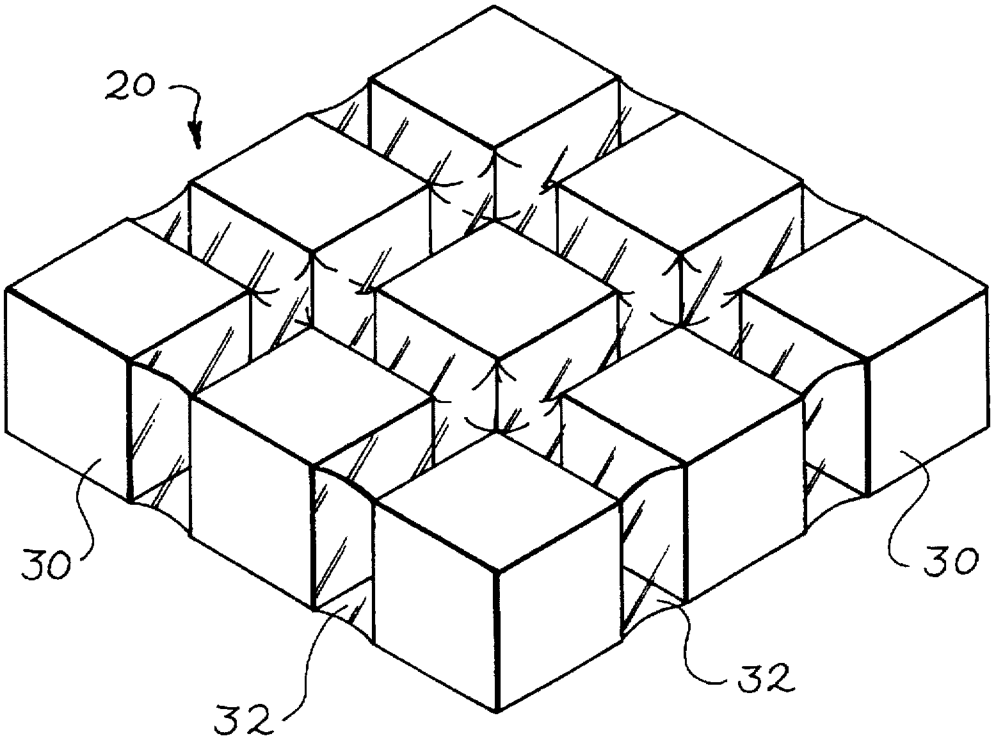
FIG. 6 is a fragmentary perspective view showing a portion of the transducer elements of the transducer array of FIG. 3.

FIG. 6 is a fragmentary perspective view showing a portion of the transducer array 20. The transducer elements 30 are shown in FIG. 6 in a two-dimensional matrix, and adjacent transducer elements 30 are isolated from one another by a filler material 32. The dimensions of individual transducer elements 30 are preferably selected as appropriate for the desired operating frequency, the frequency constant of the transducer elements 30, and the dimensions of the active transducer elements. The upper and lower faces of the array 20 are preferably plated with a suitable conductive metal to form the azimuth electrodes 26 and the elevation electrodes 28 (not shown in FIG. 6).

In this case, the transducer array comprises a 1–3 composite array of transducer elements 30 embedded in a suitable filler material 32. By way of example, the transducer elements 30 may be formed of a relaxor ferroelectric material such as PMN-PT, and may be arranged as an array of posts embedded in the filler material 32. The illustrated structure preferably uses a polymer such as an RTV silicone for the filler material 32, which acts as an electrical and acoustic insulator, and which provides a desired degree of flexibility to the array 20. This arrangement provides three advantages: (1) it allows the transducer array 20 to be shaped into the desired concave elevation curvature easily; (2) it provides mechanical isolation between the adjacent transducer elements 30; and (3) it provides efficient coupling of ultrasound energy into the volume being scanned.

It should be understood that this invention is not limited to 1–3 composite arrays, but can be also implemented in other geometrical arrangements, including 2—2 composite arrays for example. Other field-induced piezoelectric materials may be used, such as PLZT and PSnZT. Also, the filler material 32 may include other materials, including various types of epoxies and air.

Figure 7:
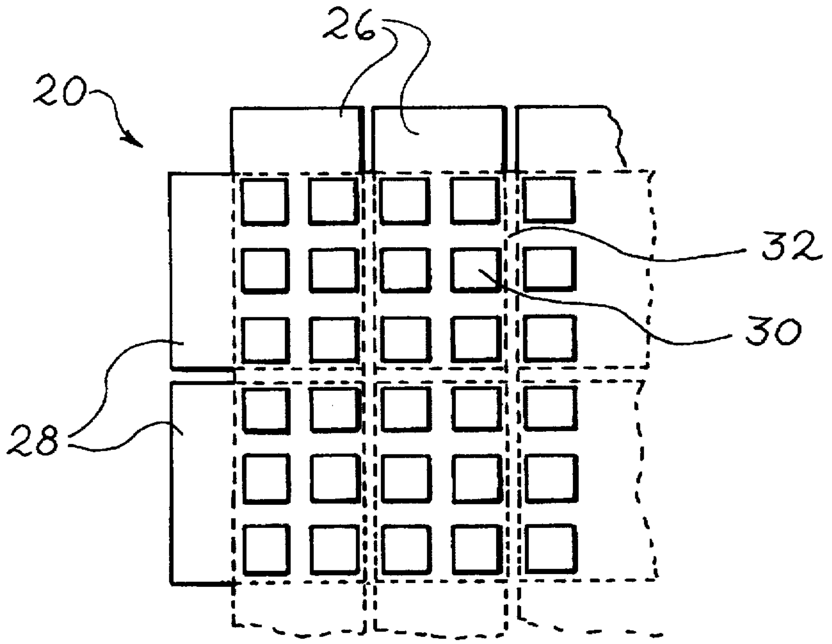
FIG. 7 is a schematic view showing the spatial arrangement of selected ones of the azimuth electrodes, elevation electrodes and transducer elements in the transducer array of FIG. 3.

FIG. 7 is a schematic view which shows a preferred arrangement among the azimuth electrodes 26, the elevation electrodes 28, and the transducer elements 30. As shown in FIG. 7, the separations between adjacent electrodes 26, 28 are preferably aligned with the filler material 32. In this way, the transducer elements 30 are completely covered by respective ones of the azimuth electrodes 26 at one end, and respective ones of the elevation electrodes 28 at the other end. In the example of FIG. 7, each azimuth electrode 26 has a width corresponding to two adjacent columns of transducer elements 30, and each elevation electrode 28 has a width corresponding to three adjacent rows of transducer elements 30. The cross-hatched transducer elements 30 are activated as a group when the respective azimuth and elevation electrodes 26, 28 are activated. Thus, the cross-hatched transducer elements 30 will transmit an ultrasound pressure wave if the azimuth electrode 26 is pulsed and the associated elevation electrode 28 is biased with a DC voltage, or vice versa.

Figure 8:
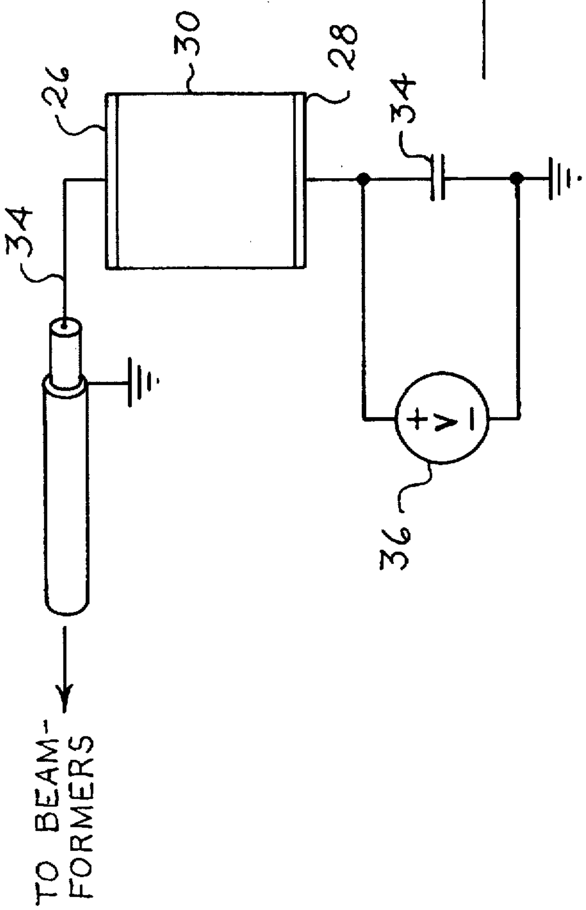
FIG. 8 is a schematic diagram showing a circuit used to energize a transducer element.

FIG. 8 provides a schematic diagram showing a circuit for operating one of the transducer elements 30. As shown in FIG. 8, the azimuth electrode 26 can operate as a signal electrode, and can be connected to transmit and receive beamformers via a conductor 34. The elevation electrode 28 can function as a control electrode, and can be coupled to signal ground via a coupling capacitor 34 and biased by a voltage source 36. FIG. 8 clearly shows the manner in which the azimuth and elevation electrodes are positioned on opposite faces of the transducer element 30, along the main resonant axis of the transducer element 30. The coupling capacitor 34 provides a low-impedance path to signal ground when the transducer element 30 is resonating.

Figure 9:
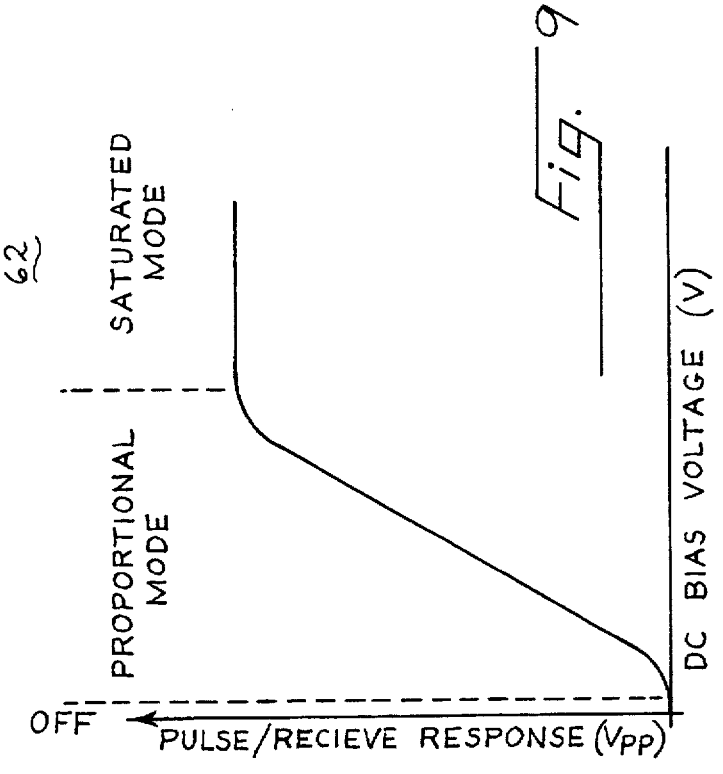
FIG. 9 is a graph showing the response of the transducer element of FIG. 8 as a function of DC bias voltage.

A characteristic feature of relaxor ferroelectric material is that the piezoelectric response of the material varies as a function of the DC bias voltage applied by the voltage source 36. FIG. 9 shows one typical response curve for relaxor ferroelectric material. As shown in FIG. 9, when the DC bias voltage is substantially equal to zero, the ferroelectric material is not active, and does not respond to applied signals (electrical or acoustic). A second mode of operation is the proportional mode, in which the piezoelectric response is proportional to the magnitude of the bias voltage. The third mode of operation is the saturated mode. Beyond a certain bias voltage (the saturation bias voltage), the piezoelectric response is maximized, and does not increase with further increases of the bias voltage.

As explained below, all three modes of operation of relaxor ferroelectric material may be exploited with the preferred embodiments. In particular, when the bias voltage is removed from a transducer element, that element is disabled, and is rendered nonresponsive to applied signals. Selected ones of the transducer elements 30 can be enabled by applying a suitable bias voltage to the associated elevation electrode. Once a bias voltage is applied and the transducer element is enabled, that transducer element will respond piezoelectrically to applied signals, to actively participate in the generation of ultrasonic energy and the sensing of echo ultrasonic energy.

It should be understood that this invention is not restricted to use with a relaxor ferroelectric material. Other piezoelectric materials such as PZT can be used. The switching design should be optimized to minimize interelement capacitive cross coupling in order to insure that the selected transducer elements can be enabled and disabled as required, which may result in an increased number of switches.

Figure 10:
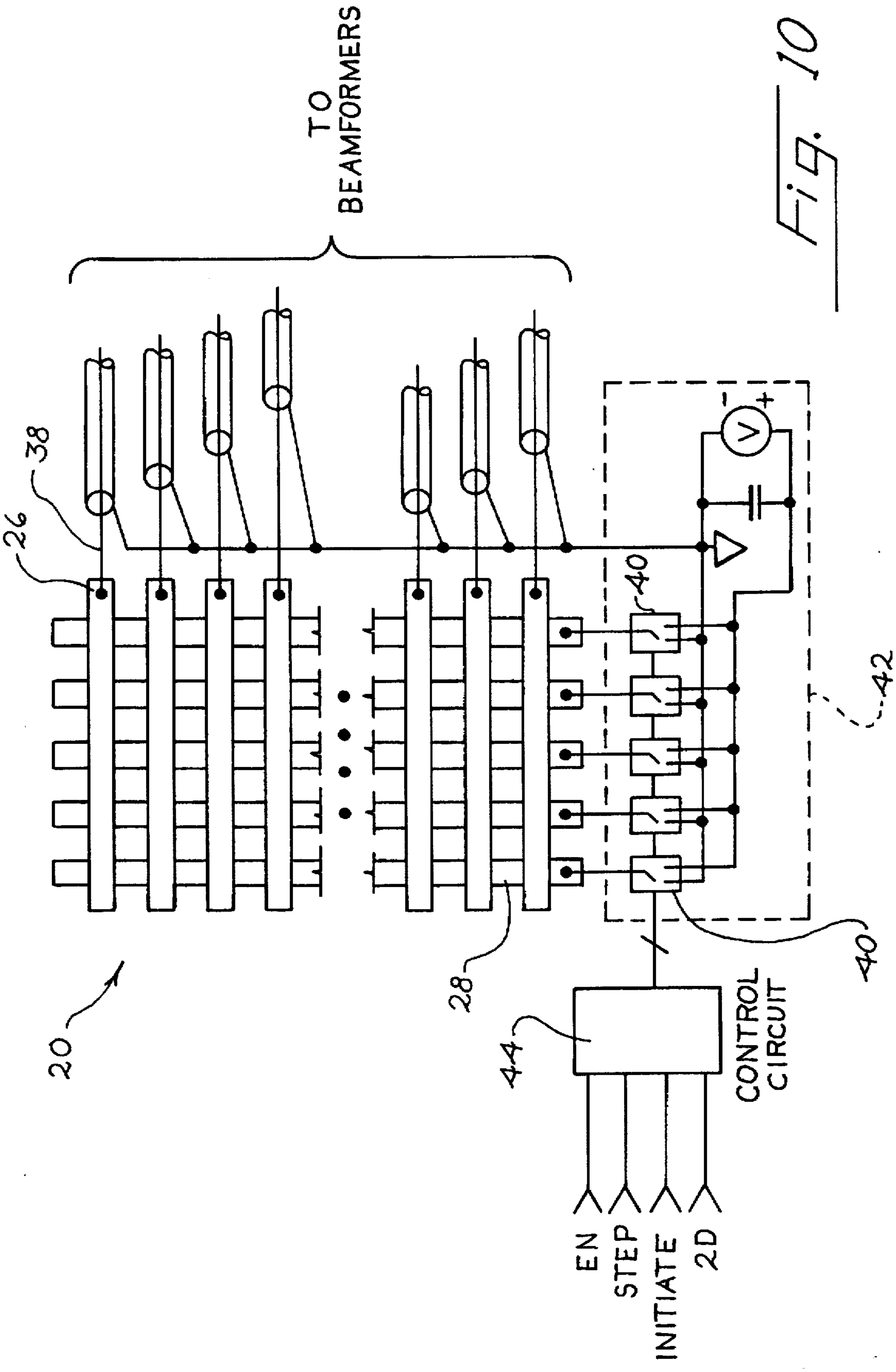
FIG. 10 is a schematic representation of a transducer array, a switching circuit, and a control circuit suitable for use in the transducer probe of FIGS. 1 and 2.

FIG. 10 is a schematic diagram that includes both a timing and a control circuit for use with the transducer array 20. Note that in FIG. 10 only five elevation electrodes 28 are shown for clarity, though in practice many more can be used as described above.

In FIG. 10, each of the azimuth electrodes 26 is connected via a respective coaxially shielded conductor 38 to the beamformers of the imaging system (not shown). Each of the elevation electrodes 28 is connected to a respective switch 40, and the switches 40 are included in a switching circuit 42. Each of the switches in this embodiment is a single-pole, double-throw switch, the state of which is controlled by a control circuit 44. Each of the switches 40 can connect the respective elevation electrode 28 either to signal ground, or to a bias voltage. In this embodiment, the bias voltage is preferably selected to be in the saturation region. As explained above, when one of the switches 40 connects the respective elevation electrode 28 to ground, all of the transducer elements associated with that elevation electrode 28 are disabled, and they produce no response to signals on the conductors 38. Conversely, when one of the switches 40 connects the respective elevation electrode 28 to the bias voltage, the transducer elements associated with that elevation electrode 28 are enabled, and respond in the well-known manner to signals on the conductor 38.

Figure 11:
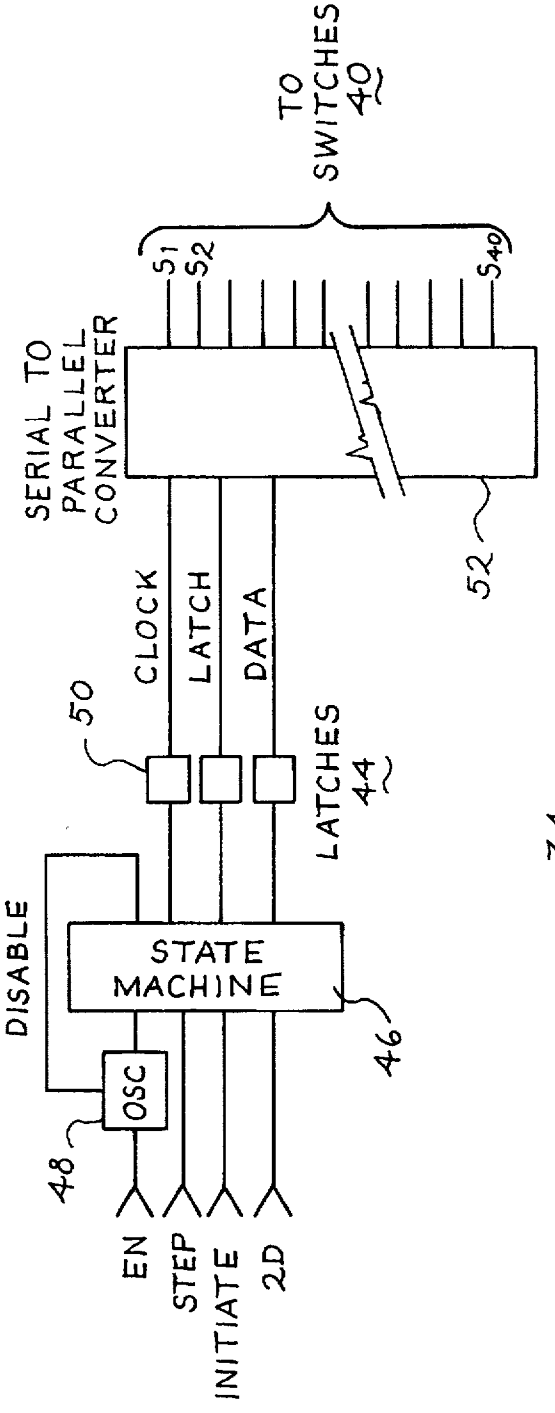
FIG. 11 is a more detailed schematic diagram of the control circuit of FIG. 10.

The control circuit 40 is preferably a shift logic state machine having four inputs: Enable, Initiate, Step and 2D. FIG. 11 a more detailed diagram of the control circuit 44. The control circuit 44 includes a logic state machine 46 which is driven by an astable oscillator 48. When an enable signal appears at the appropriate input, the astable oscillator provides a clocking signal to the logic state machine 46, which causes it to respond to either the step signal, the initiate signal, or the 2D signal, if present. The logic state machine 46, when it has finished processing the applied signals, then gates the oscillator 48 to the off state, thereby insuring that the oscillator 48 only runs while the elevation aperture is being changed. Since the elevation aperture is typically changed only between data collection frames, the control circuit 44 is inactive, and the oscillator 48 is off, during the data collection time period. In this way, electronic noise associated with the control circuit 44 is eliminated during data collection.

In response to a control signal on the initiate and enable inputs, the logic state machine latches an initial set of signals in the latches 50, thereby applying clock, latch and data signals to a serial to parallel converter 52. The signal to parallel converter 52 includes a number of outputs, each of which is connected to a respective one of the switches 40. The outputs of the serial to parallel converter act as. switch control signals, and are labeled $S_1$ through $S_{40}$ in this example. The serial to parallel converter 52 greatly reduces the number of control lines from the state machine 46.

When the enable and the step inputs are simultaneously present, the logic state machine 46 updates the data in the latches 50, and thereby causes a new set of switch control signals to be applied at the outputs of the serial to parallel converter 52.

Table 1 provides an example of one arrangement for the switch control signals. In this example there are 40 elevation electrodes, 40 switches, and 40 switch control signals $S_1$, $S_2$, . . . $S_{40}$. In this example, each elevationally steered image plane is associated with a set of eight adjacent elevation electrodes. In Table 1, the symbol 1 is used to indicate a switch control signal which causes the associated switch to connect the associated elevation electrode to bias voltage (thereby enabling the associated transducer elements), and the symbol 0 is used to indicate a switch control signal which causes the associated switch to connect the respective elevation electrode to ground (thereby disabling the associated transducer elements).

TABLE 1

| Control Signal | Switch Control Signals | | | | | | | | | | | | | | | | | | | | |
|---|---|---|---|---|---|---|---|---|---|---|---|---|---|---|---|---|---|---|---|---|---|
| Input | $S_1$ | $S_2$ | $S_3$ | $S_4$ | $S_5$ | $S_6$ | $S_7$ | $S_8$ | $S_9$ | $S_{10}$ | $S_{11}$ | . | . | . | . | | | | | $S_{39}$ | $S_{40}$ |
| 1. Initiate | 1 | 1 | 1 | 1 | 1 | 1 | 1 | 1 | 0 | 0 | 0 | . | . | . | . | | | | | 0 | 0 |
| 2. Step | 0 | 1 | 1 | 1 | 1 | 1 | 1 | 1 | 1 | 0 | 0 | . | . | . | . | | | | | 0 | 0 |
| 3. Step | 0 | 0 | 1 | 1 | 1 | 1 | 1 | 1 | 1 | 1 | 0 | . | . | . | . | | | | | 0 | 0 |
| . . | | | | | | | | . | | | | | | | | | | | | | |
| . . | | | | | | | | . | | | | | | | | | | | | | |
| . . | | | | | | | | . | | | | | | | | | | | | | |
| 32. Step | 0 | 0 | | | | . | . | . | . | . | | | | 0 | 1 | 1 | 1 | 1 | 1 | 1 | 1 | 1 | 0 |
| 33. Step | 0 | 0 | | | | . | . | . | . | . | | | | 0 | 0 | 1 | 1 | 1 | 1 | 1 | 1 | 1 | 1 |

As shown in Table 1, this example provides 33 separate image planes. The first image plane is obtained by applying the enable and initiate signals to the logic state machine 46. In this example, this causes the first elevation aperture (made up of the transducer elements associated with eight adjacent elevation electrodes at one edge of the transducer array) to be enabled, and the remaining transducer elements to be disabled. The enabled transducer elements respond to signals supplied via the conductors 38 in the conventional manner to produce two-dimensional image information in the first image plane.

Then the step and enable input signals are applied to the logic state machine 46, which causes the switch control signals to be modified to the configuration shown in line 2 of Table 1. As before, eight consecutive switches activate eight adjacent elevation electrodes, but in this case the elevation aperture is shifted by one elevation electrode toward the center of the array. Once the new elevation aperture has been enabled, a second two-dimensional slice of image information can be obtained. The second slice has been elevationally steered to a different elevational position than the first.

Table 1 shows the manner in which repeated application of the step input causes the elevation aperture to step across the face of the transducer array. In this way, 33 separate image planes can be obtained by consecutively steering the image plane to 33 different elevation positions. In general, where the total number of elevation electrodes is N, and the number of adjacent elevation electrodes cooperating to form an elevation aperture is M, and M is less than N, then the total number of possible imaging planes is $(M-N)+1$ . In the example of Table 1 $N=40$, $M=8$, and the total number of possible imaging planes is 33.

Figure 12:
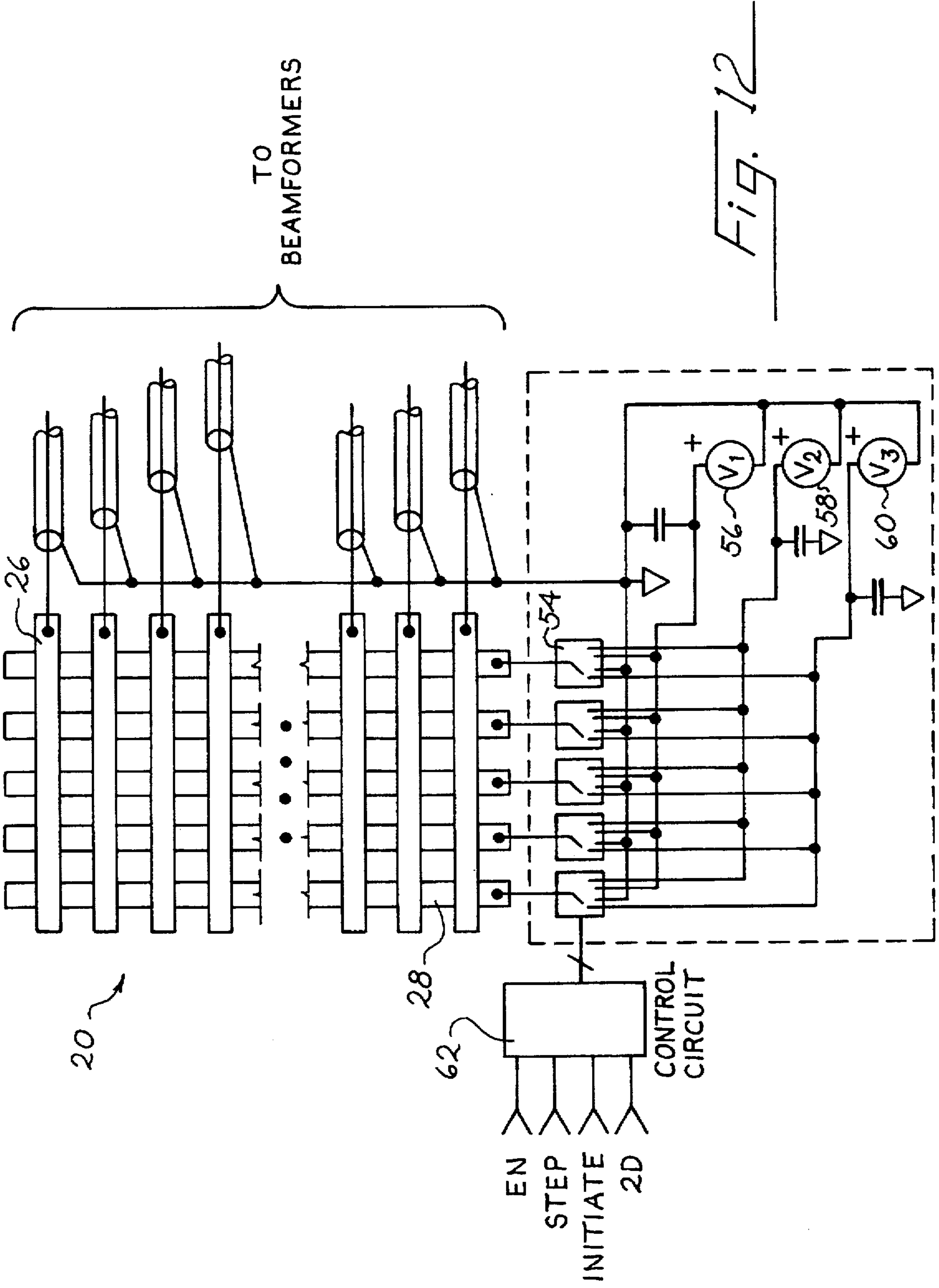
FIG. 12 is a schematic diagram showing a transducer array, a switching circuit, and a control circuit suitable for use in the transducer probe of FIGS. 1 and 12.

FIG. 12 shows an alternate embodiment for the switch and control circuits to support elevation apodization. In FIG. 12 each of the elevation electrodes 28 is connected to a respective switch 54, which in this embodiment is a single-pole, quad-throw switch. Each of the switches 54 is connected to signal ground, as described above in conjunction with FIG. 10. In addition, each of the switches 54 is connected to three separate voltage sources 56, 58, 60. Each of the sources 56, 58, 60 supplies a bias voltage at a distinctive level. For example, the bias voltages $V_1$, $V_2$, $V_3$ supplied by the voltage sources 56, 58, 60, respectively, can be arranged such that $V_1$ is less than $V_2$, and $V_2$ is less than $V_3$. Preferably, $V_3$ is substantially at saturation bias, and $V_2$ and $V_1$ are at respective levels in the proportional mode of operation of the relaxor ferroelectric material. Depending upon the state of each of the switches 54, the associated elevation electrode 28 is either at signal ground (in which case the associated transducer elements are disabled) or the electrode 28 is at one of the bias voltage levels $V_1$, $V_2$ or $V_3$ (in which case the associated transducer elements have the associated response characteristics).

Figure 13:
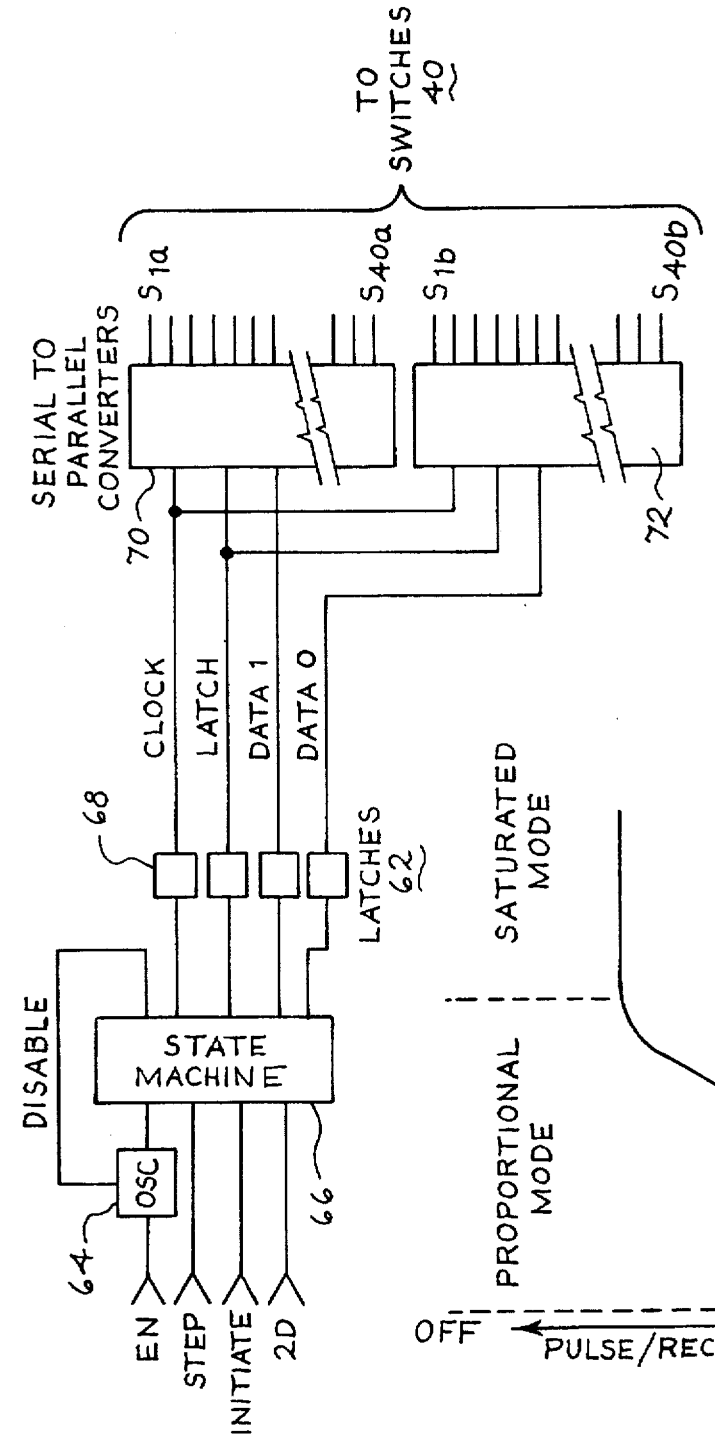
FIG. 13 is a more detailed schematic diagram of the control circuit of FIG. 12.

The circuit of FIG. 12 also includes a control circuit 62 which is shown in greater detail in FIG. 13. Turning to FIG. 13, the control circuit 62 includes an astable oscillator 64, a logic state machine 66, and latches 68 similar to those shown in FIG. 11. In this case, the logic state machine 66 supplies two data words as outputs, Data1 and Data0. Data1 is applied to a first parallel to serial converter 70, and Data0 is applied to a second parallel to serial converter 72. In this case, each of the switches 54 receives two switch control signals, one from each of the serial to parallel converters 70, 72. For example, the first switch 54 receives signals $S_{1a}$ and $S_{1b}$, and so forth.

The switch control signals supplied by the serial to parallel converters 70, 72 are selected to provide the desired elevation aperture and the desired apodization within that aperture.

For example, the logic state machine 66 can be programmed to provide the switch control signals shown in Table 2.

TABLE 2

| Control Signal | Switch Control Signals | | | | | | | | | | | | | | | | | | | | |
|---|---|---|---|---|---|---|---|---|---|---|---|---|---|---|---|---|---|---|---|---|---|
| Input | $S_1$ | $S_2$ | $S_3$ | $S_4$ | $S_5$ | $S_6$ | $S_7$ | $S_8$ | $S_9$ | $S_{10}$ | $S_{11}$ | . | . | . | . | | | | | $S_{39}$ | $S_{40}$ |
| 1. Initiate | 1 | 2 | 3 | 3 | 3 | 3 | 2 | 1 | 0 | 0 | 0 | . | . | . | . | | | | | 0 | 0 |
| 2. Step | 0 | 1 | 2 | 3 | 3 | 3 | 3 | 2 | 1 | 0 | 0 | . | . | . | . | | | | | 0 | 0 |
| 3. Step | 0 | 0 | 1 | 2 | 3 | 3 | 3 | 3 | 2 | 1 | 0 | . | . | . | . | | | | | 0 | 0 |
| . . | | | | | | | | . | | | | | | | | | | | | | |
| . . | | | | | | | | . | | | | | | | | | | | | | |
| . . | | | | | | | | . | | | | | | | | | | | | | |
| 32. Step | 0 | 0 | | | | . | . | . | . | . | | | | 0 | 1 | 2 | 3 | 3 | 3 | 3 | 2 | 1 | 0 |
| 33. Step | 0 | 0 | | | | . | . | . | . | . | | | | 0 | 0 | 1 | 2 | 3 | 3 | 3 | 3 | 2 | 1 |

In Table 2, the switch control signals are labeled $S_1$, $S_2$, $S_3$, . . . $S_{40}$, but in this case each of the switch control signals can take one of four values: 0, 1, 2, 3, as dictated by the output signals of the serial to parallel converters 70, 72. As before, the elevation aperture when initiated corresponds to the transducer elements associated with eight adjacent elevation electrodes at one side of the transducer array. However, in this case the eight enabled elevation electrodes 28 are enabled with different selected ones of the bias voltages. For example, when the switch control signal is equal to 3, this corresponds to the highest bias voltage $V_3$, and therefore the highest response. Similarly, the switch control signal values 2 and 1 correspond to the bias voltages $V_2$ and $V_1$, which are progressively lower. In this way, the transducer elements 30 near the edge of the elevation aperture are provided with a lower response than are those near the center of the aperture. As shown in Table 2, consecutive step signals step the elevation aperture across the face of the transducer array 20, while providing apodization as discussed above for each aperture.

Of course, it should be understood that the foregoing apodization has been described merely by way of illustration. A greater or lesser number of voltage sources can be used, and the particular apodization pattern that is selected can vary widely, depending on the application. If desired, the apodization pattern can vary from one elevation aperture to another. Furthermore, though an elevation aperture of eight elevation electrodes 28 has been described by way of example, it should be recognized that either a greater or lesser number of elevation electrodes may be included within the aperture, and that the elevation electrodes within the aperture do not need to be adjacent to one another in all cases.

The control circuits of FIGS. 11 and 13 are provided with a fourth input, labeled 2D, which causes the logic state machine to enable a fixed, central elevation aperture for conventional, two-dimensional scanning.

In the preferred embodiments discussed above, the imaging system transmits and receives ultrasound information as it would with a conventional, single imaging plane transducer array. Images may be collected for normal two-dimensional images by keeping the imaging aperture in one place, typically in the center of the transducer array. Three-dimensional image plane data can be collected using the following method.

First, the user positions the transducer probe over the region of interest using the normal 2D mode and then closes a switch indicating to the probe control system that three-dimensional collection should be initiated. The probe control system then controls the enable and initiate inputs to activate a first elevation imaging aperture at one edge of the transducer array. A frame of data is then collected from this elevation aperture and, before the next frame collection cycle begins, the aperture is automatically shifted by one elevation electrode, as discussed above in conjunction with Tables 1 and 2. The elevation aperture is progressively stepped across the face of the transducer array until the final elevation aperture is used to collect the final frame of data. At this point, the probe can be requested to return to the normal two-dimensional collection mode or can continue collecting information in the three-dimensional mode discussed above. Of course, it is not essential in all embodiments that consecutive elevation apertures be adjacent to one another. If desired, elevation apertures can be selected freely from available apertures in any appropriate order.

The external circuit that supplies the input signals to the logic state machines can be as simple as a push button logic circuit operated directly by the user or as complicated as a three-dimensional data collection computer system.

If desired, the control circuits discussed above can be implemented in other ways, as for example by using a microcontroller that supports static instruction execution. This type of microcontroller can be clocked by an astable oscillator as discussed above, making it possible for the microcontroller to be shut off entirely when it is not switching the elevation aperture, thereby substantially eliminating undesirable electronic noise during data acquisition.

Figure 14:
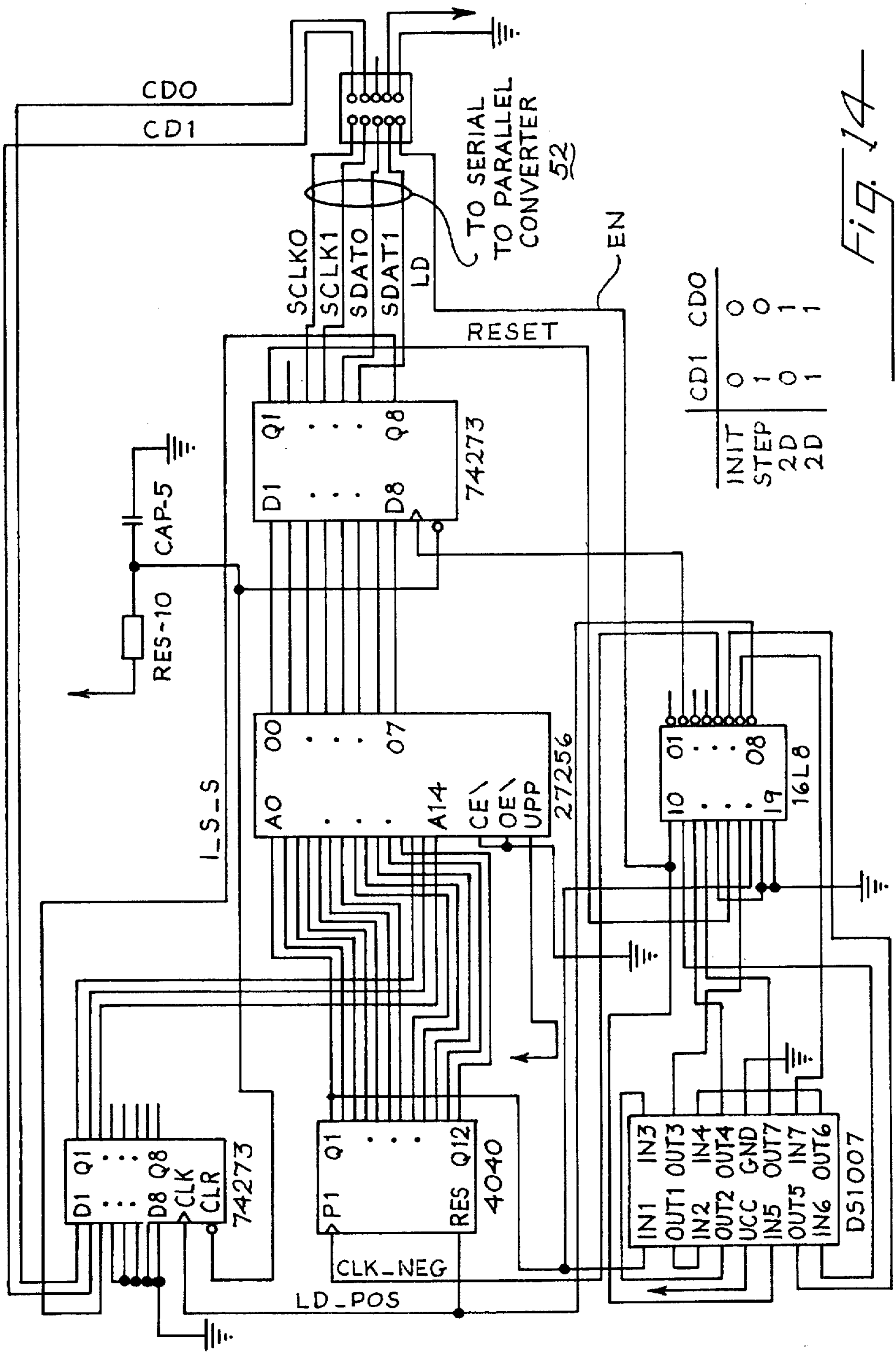
FIG. 14 is a detailed schematic diagram of the control circuit 44 of FIG. 10.
Figure 15:
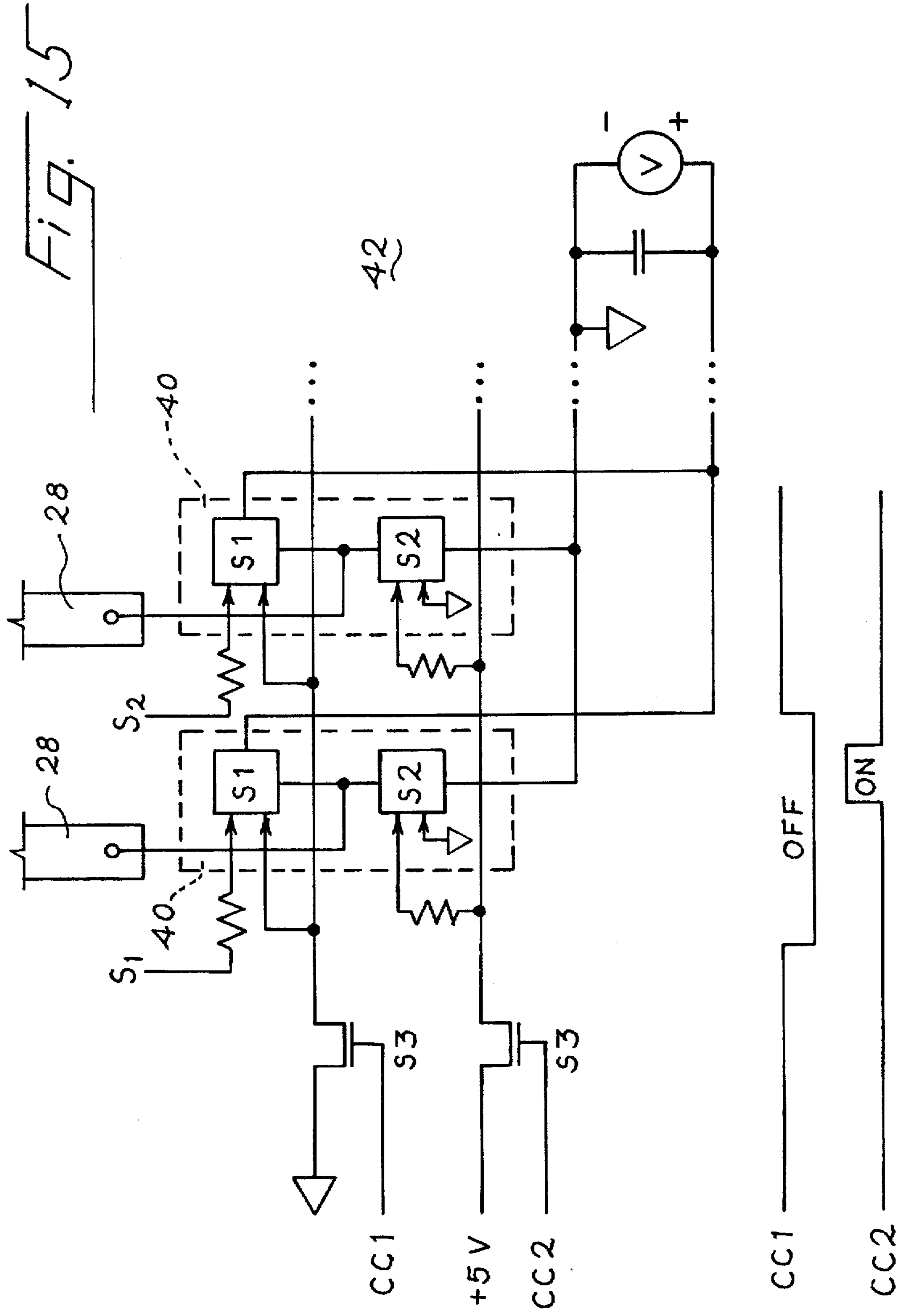
FIG. 15 is a detailed schematic diagram of one of the switching circuit 42 of FIG. 10.

The following details of construction are provided to illustrate one specific example of the transducer array 20, the control circuit 44 and the switching circuit 42. This example is not intended to limit the scope of the claimed invention in any way. Dimensions for the array 20 may be as defined in Table 3. The piezoelectric ceramic may be 0.91 PMN–0.09 PT. relaxor ferroelectric material (TRS Ceramics, Inc., State College, Pa.), and the electrodes 26, 28 may be formed of electroless nickel. The filler material 32, the backing element 22 and other conventional components such as acoustic matching layers and acoustic stack glue may be as described in U.S. Pat. No. 5,415,175, assigned to the assignee of the present invention. The control circuit 44 may be constructed as shown in FIG. 14, and the switching circuit 42 may be constructed as shown in FIG. 15. Table 4 identifies electronic components, and Table 5 provides the programming for IC5 of FIG. 14.

As shown in FIG. 15, the switches S1 selectively activate individual elevation electodes, and the switches S2 discharge the bias voltage. Preferably, the switches S2 of FIG. 15 are connected to ground only long enough to discharge the bias voltage, and are left in an open circuit configuration during electrode activation via the switches S1 and subsequent data collection.

TABLE 3

| | |
|---|---|
| Elevation Radius of Curvature: | 15 mm |
| Number of Active Elevation Elements: | 40 |
| Number of Active Azimuthal Elements: | 128 |
| Total Number of Elevation Elements: | 46 (3 inactive elements each side) |
| Total Number of Azimuthal Elements: | 138 (5 inactive elements each side) |
| Elevation Pitch: | 0.5052 mm |
| Elevation Sub Pitch: | 0.1684 mm |
| Azimuthal Pitch: | 0.30 mm |
| Azimuthal Sub Pitch: | 0.150 mm (each element consists of 6 posts) |
| Active Elevation Aperture: | 8 elements (4 mm active aperture) |
| Total Number of Image Planes: | 33 |
| Degree Step per Image Plane: | 1.93 degree |
| Dicing Blade Width (Kerf Width): | 0.030 mm |
| Ceramic Thickness: | Grind to 7.0 MHz resonant frequency |
| Lens: | ~0.28 mm constant thickness RTV silicone or urethane |

TABLE 4

| Electronic Component | Identification |
|---|---|
| IC1, IC4 | 74LS273 |
| IC2 | 74HC4040 |
| IC3 | 27C256 100 ns EPROM |
| IC5 | 16V8 PLD |
| IC6 | DS 1007S-10 Dallas |

TABLE 4-continued

| Electronic Component | Identification |
|---|---|
| | Semiconductor Delay IC |
| 52 | NJU 3718 Serial to Parallel Converter |
| S1, S2 | PVA 3354 Int'l Rectifier Solid State Relay |
| S3 | IRFL 210 Int'l Rectifier MOSFET Switch |

TABLE 5

```
/** Inputs **/
Pin 1 = LD ; /* from system */
Pin 2 = DEL_LD ; /* from delay chip */
Pin 3 = DEL_CLK ; /* from delay chip */
Pin 4 = DEL_LD_NEG; */ from delay chip */
Pin 6 = D2 ; /* RESET signal */
Pin 7 = CP2_DEL ; /* from delay chip via hc4040 */
Pin 8 = CP2 ; /* from hc4040 count out bit 0 */
/** Outputs **/
Pin 19 = LD_POS ; /* latch sta signals and reset hc4040 */
Pin 18 = LD_NEG ; /* to the delay chip */
Pin 17 = CLK_POS ; /* to delay and ls374 output latch */
Pin 16 = CLK_NEG ; /* increment hc4040 */
Pin 15 = Q1 ; /* not used */
Pin 14 = DLN1 ; /* not used */
Pin 13 = DELAY2 ; /* not used */
/** Declarations and Intermediate Variable Definitions **/
/** FORM THE CLOCK AND INPUTS FOR THE RS FLIP FLOP **/
A2 = DLN1 & ! (D2 & (!CP2_DEL & CP2));
B2 = ! (!/D2 & (!CP2_DEL & CP2));
/** Logic Equations **/
/** POSITIVE AND FOR LATCH SIGNAL AS BOTH INPUTS ARE
    ACTIVE LOW AND OUTPUT IS ACTIVE LOW **/
/** DELAY2 is used to slow down the clock frequency to provide
    for more slack to the counter an EPROM **/
LD_POS = !LD & DEL_LD;
LD_NEG - !(!LD & DEL_LD);
Q1 = ! (A2 &. ! (B2 & Q1));
DLN1 = DEL_LD_NEG;
DELAY2 = ! (Q1 & DEL_CLK);
CLK_NEG = !DELAY2;
CLK_POS = !CLK_NEG;
```

It should be apparent that the switching circuits described above operate as a means for activating selected adjacent elevation electrodes, and as a means for enabling selected transducer elements. The present invention can use many types of switches known to those in the art to implement the switching functions described above. As pointed out above, in some embodiments (as, for example, embodiments using transducer elements of PZT or other non-relaxer ferroelectric materials) the switching circuits may switch individual elevation electrodes between no connection and ground, thereby avoiding the need for voltage sources.

It should also be apparent that the disclosed control circuits enable a plurality of sets of transducer elements, wherein each set is associated with a respective elevation steering direction. This allows a user, by electronically selecting the desired set, to automatically obtain the desired elevation steering direction.

As pointed out above, the transducer array 20 is provided with a means for focusing ultrasonic energy radiated by the transducer elements in the elevation direction. In the embodiment described above this focusing means includes the backing element which holds the transducer elements in the desired concave shape. Of course, other arrangements can be used to obtain the desired focusing of ultrasonic energy in the elevation direction, including delay elements that provide the desired delay in order to obtain elevation focusing and lenses.

It should be appreciated from the foregoing that the preferred embodiments described above provide a number of important advantages. They can be used with conventional beamformers to obtain imaging information across a three-dimensional region, without increasing the complexity of the beamforming signals. In fact, no increase in the total number of beamforming signals is required in the embodiments discussed above. The transducer probes described above can be used in both the conventional two-dimensional imaging mode and in a three-dimensional imaging mode, using the same beamforming signals. Size and complexity of the transducer probe are not substantially increased, and there is no adverse electronic noise associated with changes in the elevation aperture, Of course, it should be understood that a wide range of changes and modifications can be made to the preferred embodiments described above. It is intended that the foregoing detailed description be regarded as an illustration of several forms that the invention can take, and not as a limitation of the invention. It is only the following claims, including all equivalents, which are intended to define the scope of this invention.

We claim:

1. An ultrasonic transducer array comprising:

a plurality of transducer elements distributed in both an azimuth and an elevation direction, said transducer elements arranged to form a cylindrically concave shape along the elevation direction for elevation steering;

a plurality of azimuth electrodes, each azimuth electrode coupled to a respective plurality of the transducer elements extending along the elevational direction; and a plurality of elevation electrodes, each elevation electrode coupled to a respective plurality of the transducer elements extending along the azimuth direction.

2. The invention of claim 1 further comprising:

a switching circuit coupled to the elevation electrodes to enable selected sets of the transducer elements extending along the azimuth direction via the elevation electrodes.

3. An ultrasonic transducer comprising:

a plurality of transducer elements distributed in both an azimuth and an elevation direction, said transducer elements comprising a relaxor ferroelectric, material;

a focusing system coupled to the transducer elements and operative to focus ultrasonic energy radiated by the transducer elements in the elevation direction, said focusing system comprising a backing element shaped to hold the transducer elements in a concave shape along the elevation direction; and a switching circuit coupled to the transducer elements, said switching circuit operative to enable selected sets of the transducer elements extending along the azimuth direction, said switching circuit cooperating with said focusing system to steer ultrasonic energy radiated by the transducer elements in the elevation direction.

4. The invention of claim 3 further comprising:

a plurality azimuth electrodes, each azimuth electrode coupled to a respective plurality of the transducer elements extending along the elevational direction; and a plurality of elevation electrodes, each elevation electrode coupled to a respective plurality of the transducer elements extending along the azimuth direction.

5. The invention of claim 4 wherein the switching circuit comprises a voltage source and a plurality of switches, each switch interconnected between the voltage source and a respective one of the elevation electrodes, said voltage source providing a bias voltage to the transducer elements via the elevation electrodes when the respective switches are closed.

6. The invention of claim 4 wherein the switching circuit comprises a plurality of voltage sources, each voltage source supplying a respective bias voltage; and a plurality of switches, each switch interconnected between the voltage sources and a respective one of the elevation electrodes, said switches providing selected ones of the bias voltages to selected ones of the transducer elements via the elevation electrodes to enable and apodize the selected transducer elements.

7. An ultrasonic transducer/beamformer system comprising:

a plurality of transducer elements distributed in both an azimuth and an elevation direction;

a plurality azimuth electrodes, each azimuth electrode coupled to a respective plurality of the transducer elements extending along the elevational direction;

a plurality of elevation electrodes, each elevation electrode coupled to a respective plurality of the transducer elements extending along the azimuth direction;

a focusing system coupled to the transducer elements and operative to focus ultrasonic energy radiated by the transducer elements in the elevation direction, said focusing system comprising a backing element shaped to hold the transducer elements in a concave shape along the elevation direction;

a switching circuit coupled to the elevation electrodes, said switching circuit operative to activate selected adjacent ones of the elevation electrodes to enable sets of the transducer elements coupled to the selected elevation electrodes, and thereby to steer ultrasonic energy radiated by the transducer elements in the elevation direction; and beamformer supplying beamforming signals to the azimuth electrodes, said beamforming signals effective to operate the transducer elements in both a two dimensional imaging mode and a three dimensional imaging mode without alteration of the beamforming signals.

8. The invention of claim 7 or 2 wherein the transducer elements comprise a relaxor ferroelectric material, and wherein the switching circuit comprises a voltage source and a plurality of switches, each switch interconnected between the voltage source and a respective one of the elevation electrodes, said voltage source providing a bias voltage to the transducer elements via the elevation electrodes when the respective switches are closed.

9. The invention of claim 7, 2 or 4 wherein each set of the transducer elements extending along the azimuth direction is associated with a plurality of adjacent elevation electrodes.

10. The invention of claim 9 further comprising a control circuit coupled to the switching circuit, said control circuit sequentially controlling the switching circuit to enable a plurality of said sets, each set associated with a respective elevation steering direction.

11. The invention of claim 7 or 2 wherein the transducer elements comprise a relaxor ferroelectric material; and wherein the switching circuit comprises a plurality of voltage sources, each voltage source supplying a respective bias voltage; and a plurality of switches, each switch interconnected between the voltage sources and a respective one of the elevation electrodes, said switches providing selected ones of the bias voltages to selected ones of the transducer elements via the elevation electrodes to enable and apodize the selected transducer elements.

12. An ultrasonic transducer comprising:

a plurality of transducer elements distributed in both an azimuth and an elevation direction;

means for holding the transducer elements in a cylindrically concave shape along the elevation direction for elevation steering; and means for enabling selected ones of the transducer elements to steer ultrasonic energy radiated by the selected transducer elements in the elevation direction.

13. The invention of claim 12 further comprising:

a plurality azimuth electrodes, each azimuth electrode coupled to a respective plurality of the transducer elements extending along the elevation direction; and a plurality of elevation electrodes, each elevation electrode coupled to a respective plurality of the transducer elements extending along the azimuth direction.

14. The invention of claim 1 or 3 or 7 or 12 wherein the transducer elements comprise a relaxor ferroelectric material.

15. The invention of claim 14 wherein the transducer elements comprise a 1–3 composite array.

16. An ultrasonic transducer comprising:

a plurality of transducer elements distributed in both an azimuth and an elevation direction, said transducer elements comprising a relaxor ferroelectric material;

a plurality azimuth electrodes, each azimuth electrode coupled to a respective plurality of the transducer elements extending along the elevational direction;

a plurality of elevation electrodes, each elevation electrode coupled to a respective plurality of the transducer elements extending along the azimuth direction;

means for holding the transducer elements in a concave shape along the elevation direction; and means for activating selected adjacent ones of the elevation electrodes to enable the transducer elements coupled to the selected elevation electrodes and thereby to steer ultrasonic energy radiated by the transducer elements in the elevation direction.

* * * * *

UNITED STATES PATENT AND TRADEMARK OFFICE

CERTIFICATE OF CORRECTION

PATENT NO. : 5,671,746

DATED : September 30, 1997

INVENTOR(S) : William R. Dreschel et al.

It is certified that error appears in the above-indentified patent and that said Letters Patent is hereby corrected as shown below:

In the Claims

In claim 4, line 2, after "plurality" insert --of--.

In claim 7, line 5, after "plurality" insert --of--.

In claim 13, line 2, after "plurality" insert --of--.

In claim 16, line 5, after "plurality" insert --of--.

Signed and Sealed this

Twenty-second Day of June, 1999

*Attest:*

Q. TODD DICKINSON

*Attesting Officer*

*Acting Commissioner of Patents and Trademarks*